US008101207B2

(12) United States Patent
Miura et al.

(10) Patent No.: US 8,101,207 B2
(45) Date of Patent: Jan. 24, 2012

(54) COMPOSITION CONTAINING MEDICINE EXTREMELY SLIGHTLY SOLUBLE IN WATER AND METHOD FOR PREPARATION THEREOF

(75) Inventors: Hiroshi Miura, Fuji (JP); Makoto Kanebako, Shizuoka (JP); Masayuki Kanishi, Numadu (JP); Yasuo Shinoda, Shizuoka (JP); Toshio Inagi, Mishima (JP); Hirofumi Takeuchi, Gifu (JP)

(73) Assignee: Kowa Co., Ltd., Nagoya-shi (JP)

( * ) Notice: Subject to any disclaimer, the term of this patent is extended or adjusted under 35 U.S.C. 154(b) by 601 days.

(21) Appl. No.: 10/551,901

(22) PCT Filed: Apr. 28, 2004

(86) PCT No.: PCT/JP2004/006141
§ 371 (c)(1),
(2), (4) Date: Oct. 4, 2005

(87) PCT Pub. No.: WO2004/096280
PCT Pub. Date: Nov. 11, 2004

(65) Prior Publication Data
US 2007/0128273 A1 Jun. 7, 2007

Related U.S. Application Data

(60) Provisional application No. 60/466,069, filed on Apr. 29, 2003.

(51) Int. Cl.
*A61K 9/20* (2006.01)
*A61K 47/02* (2006.01)
*A61K 47/04* (2006.01)
*A61K 31/50* (2006.01)

(52) U.S. Cl. .......................... 424/489; 424/464; 514/247
(58) Field of Classification Search .................. 424/489; 514/161, 171, 247, 252, 423
See application file for complete search history.

(56) References Cited

U.S. PATENT DOCUMENTS

| 5,236,906 | A | * | 8/1993 | Yamamoto | 514/171 |
| 5,538,728 | A | * | 7/1996 | Yanaki et al. | 424/401 |
| 5,851,453 | A | | 12/1998 | Hanna et al. | |
| 6,348,468 | B1 | * | 2/2002 | Ohkuchi et al. | 514/252.03 |
| 2002/0047058 | A1 | * | 4/2002 | Verhoff et al. | 241/26 |
| 2003/0121453 | A1 | * | 7/2003 | Iwahashi et al. | 106/502 |
| 2003/0220204 | A1 | * | 11/2003 | Baran et al. | 507/200 |
| 2004/0058956 | A1 | * | 3/2004 | Akiyama et al. | 514/318 |

FOREIGN PATENT DOCUMENTS

| EP | 1 323 786 A1 * | 7/2003 |
| JP | 61-227520 * | 10/1986 |
| JP | 6-0404714 | 2/1994 |
| JP | 8-511987 | 12/1996 |
| JP | 2000-198776 | 7/2000 |
| JP | 2002-302435 | 10/2002 |
| JP | 2002-345940 | 12/2002 |
| JP | 2002-345950 * | 12/2002 |
| WO | 02/20624 | 3/2002 |
| WO | 02/051381 | 7/2002 |
| WO | 02/060411 | 8/2002 |

OTHER PUBLICATIONS

Website: www.sigma-aldrich.com (silica gel product 403563).*
Website: www.sigma-aldrich.com (silica gel product No. 403563).*
U.S. Patent Documents—None.*
Non-Patent Documents—None.*
U.S. Appl. No. 10/554,921, filed Oct. 31, 2005, Miura, et al.
U.S. Appl. No. 11/813,968, filed Jul. 13, 2007, Miura, et al.
David D. Hile et al., Active growth delivery from poly (D, L-lactide-co-glycolide) foams prepared in supercritical CO2, Journal of Controlled Release, vol. 66, pp. 177 to 185, 2000.
Petra Sencar-Bozic et al., Improvement of nifedipine dissolution characteristics using supercritical CO2, International Journal of Pharmaceutics, vol. 148, pp. 123 to 130, 1997.
"Design and Evaluation of Oral Preparation", Editor: Mitsuru Hashida, Jiho, Inc., Feb. 10, 1995, pp. 172-185 (with partial English translation).
Donald C. Monkhouse, et al., "Use of Adsorbents in Enhancement of Drug Dissolution I", Journal of Pharmaceutical Sciences, vol. 61, No. 9, Sep. 1972, pp. 1430-1435.
Donald C. Monkhouse, et al., "Use of Adsorbents in Enhancement of Drug Dissolution II", Journal of Pharmaceutical Sciences, vol. 61, No. 9, Sep. 1972, pp. 1435-1441.
K. Y. Yang, et al., "Effects of Amorphous Silicon Dioxides on Drug Dissolution", Journal of Pharmaceutical Sciences, vol. 68. No. 5, May 1979, pp. 560-565.
Concha Domingo, et al., "Organic-Guest/Microporous-Host Composite Materials Obtained by Diffusion from a Supercritical Solution", Advanced Materials, vol. 10, No. 9, 1998, pp. 672-676.
C. Magnan, et al., "Impregnation of Porous Supports with Active Substances by Means of Supercritical Fluids", Process Technol Proc, High Pressure Chemical Engineering, vol. 12, 1996, pp. 509-514.
C. Domingo, et al., "Study Adsorption Processes of Model Drugs at Supercritical Conditions Using Partial Least Squares Regression", Analytica Chimica Acta, vol. 452, No. 2, 2002, pp. 311-319.
C. Domingo, et al., "Application of Chemometric Techniques to the Characterisation of Impregnated Materials Obtained Following Supercritical Fluid Technology", The Analyst, vol. 126, No. 10, 2001, pp. 1792-1796.
Office Action issued Aug. 17, 2010, in Japanese Patent Application No. 2005-505928 (with English-language Translation).

* cited by examiner

*Primary Examiner* — Robert A Wax
*Assistant Examiner* — Jeffrey T Palenik
(74) *Attorney, Agent, or Firm* — Oblon, Spivak, McClelland, Maier & Neustadt, L.L.P.

(57) ABSTRACT

A composition containing a very low water-soluble drug, which composition is produced by treating, with a supercritical or subcritical carbon dioxide fluid, a mixture containing a very low water-soluble drug and a porous material (exclusive of a porous silica material characterized in that the material has an average pore diameter of 1 to 20 nm, the total pore volume of the material that have a diameter falling within a range of ±40% of the average pore diameter account for 60% or more the volume of all the pores of the material, and, when subjected to X-ray diffractometry, the material exhibits one or more peaks at a diffraction angle ($2\theta$) corresponding to d of 1 nm or more); and a method for producing the composition. The very-low-water-soluble-drug-containing composition of the present invention ensures improved dissolution of the very low water-soluble drug.

16 Claims, No Drawings

COMPOSITION CONTAINING MEDICINE EXTREMELY SLIGHTLY SOLUBLE IN WATER AND METHOD FOR PREPARATION THEREOF

TECHNICAL FIELD

The present invention relates to a composition containing a drug having very low solubility in water (hereinafter the drug will be referred to as a "very low water-soluble drug"), the drug exhibiting improved dissolution; and to a method for producing the composition.

BACKGROUND ART

It is known that 2-benzyl-5-(4-chlorophenyl)-6-[4-(methylthio)phenyl]-2H-pyridazin-3-one exhibits excellent effect of inhibiting production of interleukin-1β, and is useful as a preventive and therapeutic drug, for example, for immune diseases, inflammatory diseases, and ischemic diseases (Japanese Patent Application Laid-Open (kokai) No. 12-198776). However, this compound has very low solubility in water and exhibits poor dissolution from the preparation. Therefore, a demand has arisen for improvement of its dissolution.

Known techniques for improving the dissolution of a low water-soluble drug include micronization of the drug and preparation of derivatives of the drug. However, micronization does not improve the dissolution of a very low water-soluble drug such as 2-benzyl-5-(4-chlorophenyl)-6-[4-(methylthio)phenyl]-2H-pyridazin-3-one. Meanwhile, when such a drug is prepared into a derivative, the pharmaceutical activity of the drug changes. Accordingly, these techniques are not preferable.

Also, as a technique for improving dissolution, there has been proposed, for example, a method in which a physiologically active substance such as nifedipine is treated with carbon dioxide which is in a supercritical or subcritical state, or with liquid carbon dioxide (e.g., Japanese Patent Application Laid-Open (kokai) No. 2002-302435). This method improves the dissolution of a low water-soluble drug such as nifedipine, but fails to improve the dissolution of a very low water-soluble drug such as 2-benzyl-5-(4-chlorophenyl)-6-[4-(methylthio)phenyl]-2H-pyridazin-3-one.

In view of the foregoing, objects of the present invention are to provide a composition containing a very low water-soluble drug exhibiting improved dissolution, and to provide a method for producing the composition.

DISCLOSURE OF THE INVENTION

In order to attain the above objects, the present inventors have performed extensive studies, and as a result have found that when a mixture containing a very low water-soluble drug and a porous material (exclusive of a porous silica material characterized in that the material has an average pore diameter of 1 to 20 nm, the total pore volume of the material that have a diameter falling within a range of ±40% of the average pore diameter account for 60% or more the volume of all the pores of the material, and, when subjected to X-ray diffractometry, the material exhibits one or more peaks at a diffraction angle (2θ) corresponding to d of 1 nm or more) is treated with a supercritical or subcritical carbon dioxide fluid, the very low water-soluble drug contained in the resultant composition exhibits improved dissolution. The present invention has been accomplished on the basis of this finding.

Accordingly, the present invention provides a composition containing a very low water-soluble drug, which composition is produced by treating, with a supercritical or subcritical carbon dioxide fluid, a mixture containing a very low water-soluble drug and a porous material (exclusive of a porous silica material characterized in that the material has an average pore diameter of 1 to 20 nm, the total pore volume of the material that have a diameter falling within a range of ±40% of the average pore diameter account for 60% or more the volume of all the pores of the material, and, when subjected to X-ray diffractometry, the material exhibits one or more peaks at a diffraction angle (2θ) corresponding to d of 1 nm or more) (hereinafter the composition may be referred to as "very-low-water-soluble-drug-containing composition"); and a method for producing the composition.

BEST MODE FOR CARRYING OUT THE INVENTION

The very low water-soluble drug employed in the present invention has a solubility in water at 25° C. of less than 10 μg/mL, preferably less than 5 μg/mL, more preferably less than 1 μg/mL.

No particular limitations are imposed on the type of the very low water-soluble drug employed in the present invention. Examples of the very low water-soluble drug which may be employed include an antipyretic, an anti-inflammatory agent, an analgesic agent, a tranquilizer, a sedative agent, an antitumor agent, an antibacterial agent, an antibiotic, an anti-hyperlipidemic agent, an antitussive/expectorant agent, a muscle relaxant, an antiepileptic agent, an antiulcer agent, an antidepressant, an antiallergic agent, a cardiotonic agent, an arrhythmia treatment agent, a vasodilator, a hypotensive/diuretic agent, a diabetes treatment agent, an antituberculous agent, an antirheumatic agent, a narcotic antagonist, a hormone agent, a fat-soluble vitamin preparation, an anticoagulant, an ischemic disease treatment drug, an immune disease treatment drug, an Alzheimer's disease treatment drug, an osteoporosis treatment drug, an angiogenesis treatment drug, a retinopathy treatment drug, a drug for treating central (or branch) retinal vein occlusion, a drug for treating age-related disciform macular degeneration, a cerebrovascular spasm treatment drug, a cerebral thrombosis treatment drug, a cerebral infarction treatment drug, a cerebral occlusion treatment drug, an intracerebral hemorrhage treatment drug, a subarachnoid hemorrhage treatment drug, a hypertensive encephalopathy treatment drug, a drug for treating transient cerebral ischemic attack, a multi-infarct dementia treatment drug, an arteriosclerosis treatment drug, a Huntington's disease treatment drug, a drug for treating brain tissue disorder, an optic neuropathy treatment drug, a glaucoma treatment drug, an ocular hypertension treatment drug, a retinal detachment treatment drug, an arthritis treatment drug, an antisepsis drug, an antiseptic shock drug, an antiasthma drug, a pollakiuria/incontinentia treatment drug, an atopic dermatitis treatment drug, an allergic rhinitis treatment drug, a cosmetic composition, an agrichemical composition, a pesticide, a bactericide, a herbicide, compositions for foods and beverages, and compositions for animal drugs. Preferred specific examples of the very low water-soluble drug include 2-benzyl-5-(4-chlorophenyl)-6-[4-(methylthio)phenyl]-2H-pyridazin-3-one (hereinafter may be referred to simply as "compound A", 5,6-bis(4-methoxyphenyl)-2-ethyl-2H-pyridazin-3-one, 5,6-bis(4-methoxyphenyl)-2-methyl-2H-pyridazin-3-one, 5,6-bis(4-methoxyphenyl)-2-isopropyl-2H-pyridazin-3-one, 5,6-bis(4-methoxyphenyl)-2-cyclopropyl-2H-pyridazin-3-one, 5,6-bis(4-methoxyphenyl)-2- cyclopropylmethyl-2H-pyridazin-3-one, 5,6-bis(4-methoxyphenyl)-2-cyclopropylmethyl-2H-pyridazin-3-thione, 5,6-bis(4-methoxyphenyl)-2-cyclopentyl-2H-pyridazin-3-one, 5,6-bis(4-methoxyphenyl)-2-cyclopentylmethyl-2H-pyridazin-3-one, 6-(4-methoxyphenyl)-5-phenyl-2H-pyridazin-3-one, 5,6-bis(4-methoxyphenyl)-2-(4-chlorocinnamyl)-2H-pyridazin-3-one, 5,6-bis(4-methoxyphenyl)-2-benzyl-2H-pyridazin-3-one, 5,6-bis(4-methoxyphenyl)-2-(4-methoxybenzyl)-2H-pyridazin-3-one, 5,6-bis(4-methoxyphenyl)-2-(3,4,5-trimethoxybenzyl)-2H-pyridazin-3-one, 5,6-bis(4-methoxyphenyl)-2-(3-phenylpropyl)-2H-pyridazin-3-one, 5,6-bis(4-methoxyphenyl)-2-cinnamyl-2H-pyridazin-3-one, 5,6-bis(4-methoxyphenyl)-2-(4-methoxycinnamyl)-2H-pyridazin-3-one, 5,6-bis(4-methoxyphenyl)-2-[3-(4-methoxyphenyl)propyl]-2H-pyridazin-3-one, 5,6-bis(4-methoxyphenyl)-2-(4-methylcinnamyl)-2H-pyridazin-3-one, 5,6-bis(4-methoxyphenyl)-2-[3-(4-methylphenyl)propyl]-2H-pyridazin-3-one, 5,6-bis(4-methoxyphenyl)-2-(4-fluorobenzyl)-2H-pyridazin-3-one, 5,6-bis(4-methoxyphenyl)-2-(2,4-difluorobenzyl)-2H-pyridazin-3-one, 5,6-bis(4-methoxyphenyl)-2-(3-fluoro-4-methoxybenzyl)-2H-pyridazin-3-one, 5,6-bis(4-methoxyphenyl)-2-(3,4-difluorobenzyl)-2H-pyridazin-3-one, 5,6-bis(4-methoxyphenyl)-2-(4-fluorocinnamyl)-2H-pyridazin-3-one, 5,6-bis(4-methoxyphenyl)-2-(2,4-difluorocinnamyl)-2H-pyridazin-3-one, 5,6-bis(4-methoxyphenyl)-2-(4-chlorobenzyl)-2H-pyridazin-3-one, 5,6-bis(4-methoxyphenyl)-2-(3,4-dichlorobenzyl)-2H-pyridazin-3-one, 5,6-bis(4-methoxyphenyl)-2-(4-chlorophenetyl)-2H-pyridazin-3-one, 5,6-bis(4-methoxyphenyl)-2-(2,4-dichlorophenetyl)-2H-pyridazin-3-one, 5,6-bis(4-methoxyphenyl)-2-(2,4-dichlorocinnamyl)-2H-pyridazin-3-one, 5,6-bis(4-methoxyphenyl)-2-(2-pyridylmethyl)-2H-pyridazin-3-one, 5,6-bis(4-methoxyphenyl)-2-(3-pyridylmethyl)-2H-pyridazin-3-one, 5,6-bis(4-methoxyphenyl)-2-(4-pyridylmethyl)-2H-pyridazin-3-one, 6-(3,4-dimethoxyphenyl)-5-(4-methoxyphenyl)-2-(2,4-dichlorobenzyl)-2H-pyridazin-3-one, 6-(3,4-dimethoxyphenyl)-5-(4-methoxyphenyl)-2-(4-chlorophenetyl)-2H-pyridazin-3-one, 5-(4-chlorophenyl)-6-(4-methoxyphenyl)-2-benzyl-2H-pyridazin-3-one, 5-(4-chlorophenyl)-6-(4-methoxyphenyl)-2-(4-pyridylmethyl)-2H-pyridazin-3-one, 5-(4-chlorophenyl)-6-[4-(methylthio)phenyl]-2-(2,4-dichlorobenzyl)-2H-pyridazin-3-one, 5-(4-chlorophenyl)-6-[4-(methylthio)phenyl]-2-(3-pyridylmethyl)-2H-pyridazin-3-one, 5-(4-fluorophenyl)-6-[4-(methylthio)phenyl]-2-cyclopropylmethyl-2H-pyridazin-3-one, 5-(4-fluorophenyl)-6-[4-(methylthio)phenyl]-2-benzyl-2H-pyridazin-3-one, 5-(4-fluorophenyl)-6-[4-(methylthio)phenyl]-2-(4-methoxybenzyl)-2H-pyridazin-3-one, 5-(4-fluorophenyl)-6-[4-(methylthio)phenyl]-2-(2,4-dichlorobenzyl)-2H-pyridazin-3-one, 5-(4-fluorophenyl)-6-[4-(methylthio)phenyl]-2-(4-pyridylmethyl)-2H-pyridazin-3-one, 2-(4-methoxybenzyl)-6-(4-methoxyphenyl)-5-(4-pyridyl)-2H-pyridazin-3-one, 2-(4-chlorobenzyl)-6-(4-methoxyphenyl)-5-(4-pyridyl)-2H-pyridazin-3-one, 2-cyclopropylmethyl-5-(4-fluorophenyl)-6-[4-(methylsulfinyl)phenyl]-2H-pyridazin-3-one, 5-(4-chlorophenyl)-2-(2,4-dichlorobenzyl)-6-[4-(methylsulfinyl)phenyl]-2H-pyridazin-3-one, 5-(4-chlorophenyl)-2-(2,4-dichlorobenzyl)-6-[4-(methylsulfonyl)phenyl]-2H-pyridazin-3-one, 5,6-bis(4-methoxyphenyl)-2-benzyl-2H-pyridazin-3-thione, 5,6-bis(4-methoxyphenyl)-2-(4-fluorobenzyl)-2H-pyridazin-3-thione, 5,6-bis(4-methoxyphenyl)-2-(2,4-difluorobenzyl-2H-pyridazin-3-thione, 5,6-bis(4-methoxyphenyl)-2-(3-pyridylmethyl)-2H-pyridazin-3-thione, 5,6-bis(4-methoxyphenyl)-2-(2,4-difluorocinnamyl)-2H-pyridazin-3-thione, 5-(4-chlorophenyl)-2-(2,4-dichlorobenzyl)-6-[4-(methylthio)phenyl]-2H-pyridazin-3-thione, 5-(4-chlorophenyl)-6-[4-(methylthio)phenyl]-2-(3-pyridylmethyl)-2H-pyridazin-3-thione, 5-(4-fluorophenyl)-6-[4-(methylthio)phenyl]-2H-pyridazin-3-thione, 2-cyclopropylmethyl-5-(4-fluorophenyl)-6-[4-(methylthio)phenyl]-2H-pyridazin-3-thione, 2-benzyl-5-(4-fluorophenyl)-6-[4-(methylthio)phenyl]-2H-pyridazin-3-thione, 5-(4-fluorophenyl)-2-(4-methoxybenzyl)-6-[4-(methylthio)phenyl]-2H-pyridazin-3-thione, 2-(2,4-dichlorobenzyl)-5-(4-fluorophenyl)-6-[4-(methylthio)phenyl]-2H-pyridazin-3-thione, and 2-(4-chlorobenzyl)-6-(4-methoxyphenyl)-5-(4-pyridyl)-2H-pyridazin-3-thione. Of these compounds, compound A is particularly preferred.

Examples of the porous material employed in the present invention (hereinafter may be referred to simply as "the present porous material") (exclusive of a porous silica material characterized in that the material has an average pore diameter of 1 to 20 nm, the total pore volume of the material that have a diameter falling within a range of ±40% of the average pore diameter account for 60% or more the volume of all the pores of the material, and, when subjected to X-ray diffractometry, the material exhibits one or more peaks at a diffraction angle (2θ) corresponding to d of 1 nm or more) include a porous carbon material, a porous aluminum material, and a porous silicon material.

Examples of the porous carbon material include powdery activated carbon, granular activated carbon, carbon molecular sieve, activated carbon beads, fibrous activated carbon, high-surface-area activated carbon, molded activated carbon, and honeycomb activated carbon.

Examples of the porous aluminum material include alumina, aluminum oxide, activated alumina, boehmite gel, and zeolite.

Examples of the porous silicon material include porous silica materials such as light anhydrous silicic acid, hydrated silicon dioxide, silicon dioxide, magnesium aluminosilicate, calcium silicate, magnesium silicate, aluminum magnesium silicate, hydroxypropylcellulose.light anhydrous silicic acid mixture, diatomaceous earth, synthetic aluminum silicate, synthetic aluminum silicate.hydroxypropyl starch.crystalline cellulose, synthetic sodium magnesium silicate, colloidal hydrous aluminum silicate, and zeolite. These porous silicon materials exclude a porous silica material characterized in that the material has an average pore diameter of 1 to 20 nm, the total pore volume of the material that have a diameter falling within a range of ±40% of the average pore diameter account for 60% or more the volume of all the pores of the material, and, when subjected to X-ray diffractometry, the material exhibits one or more peaks at a diffraction angle (2θ) corresponding to d of 1 nm or more (hereinafter the porous silica material may be referred to simply as "porous silica material A").

The average pore diameter of the porous silica material A can be measured by means of the gas adsorption method by use of, for example, surface area and porosimetry analyzer TriStar 3000 (product of Micromeritics).

The expression "when subjected to X-ray diffractometry, the porous silica material A exhibits one or more peaks at a diffraction angle (2θ) corresponding to d of 1 nm or more" refers to the case where the porous silica material A has a periodic structure with period d corresponding to the diffraction angle; i.e., the porous silica material A has a structure in which pores are regularly arranged at intervals of 1 nm or more. Therefore, pores of the porous silica material A have a sufficiently uniform diameter.

X-ray diffractometry can be carried out by use of, for example, an automatic X-ray diffractometer system MXP3 (product of MAC Science Co., Ltd.).

The present porous material is preferably a porous silicon material. Examples of the porous silicon material include light anhydrous silicic acid, hydrated silicon dioxide, silicon dioxide, and calcium silicate. Specific examples include commercially available materials, such as Sylysia 250, Sylysia 320, Sylysia 350, and Sylysia 740 (products of Fuji Silysia Chemical Ltd.); Adsolider 101 and Adsolider 102 (products of Freund Industrial Co., Ltd.); Carplex #67 (product of Shionogi & Co., Ltd.); Aerosil 200 and Aerosil 300 (products of Nippon Aerosil Co., Ltd.); Sunsphere H-51 (product of Asahi Glass Co., Ltd.); and Florite RE (product of Eisai Co., Ltd.).

The present porous material preferably has an average pore diameter of 1 to 1,000 nm, more preferably 2 to 500 nm, particularly preferably 2 to 200 nm. The average pore diameter can be measured by means of, for example, the gas adsorption method.

The present porous material preferably has a specific surface area of 1 to 2,000 $m^2/g$, more preferably 100 to 1,800 $m^2/g$, particularly preferably 200 to 1,500 $m^2/g$. The specific surface area can be measured by means of, for example, the gas adsorption method.

In the present invention, the ratio by weight of the very low water-soluble drug to the present porous material is preferably 1:0.1 to 1:1,000, more preferably 1:0.5 to 1:100, particularly preferably 1:1 to 1:50.

The carbon dioxide employed in the present invention assumes the form of liquid, gas, or solid (dry ice).

As used herein, the term "supercritical state" refers to a state where both pressure and temperature exceed the critical point of a substance (for the case of carbon dioxide, critical pressure is about 7.38 MPa, and critical temperature is about 31.0° C.); and the term "subcritical state" refers to a state where one but not both of pressure and temperature exceeds the critical point of a substance. Critical point is described in detail in, for example, "Particle Formation with Supercritical Fluids—A Review" authored by J. W. Tom and P. G. Debenedetti, J. Aerosol Sci., 22 (5), pp. 555-584, 1991, FIG. 1.

In the present invention, the ratio by weight of the very low water-soluble drug to the supercritical or subcritical carbon dioxide fluid is preferably 1:1 to 1:1,000,000, more preferably 1:10 to 1:100,000, particularly preferably 1:50 to 1:50, 000.

In the present invention, the time for treatment with the supercritical or subcritical carbon dioxide fluid is preferably one minute to 24 hours, more preferably 0.5 to 12 hours, particularly preferably one to eight hours.

In the present invention, the vessel employed for treatment with the supercritical or subcritical carbon dioxide fluid may be, for example, a pressure-resistant vessel, a supercritical extraction system, a supercritical ultrafine powder manufacturing system, or a test apparatus for supercritical or subcritical fluid. Examples of the vessel include Portable Reactor (product of Taiatsu Techno Corporation), supercritical extraction system SCF-get (product of JASCO Corporation), and supercritical ultrafine powder manufacturing system SC Sprayer (product of Nikkiso Co., Ltd.).

In the present invention, the temperature for treatment with the supercritical or subcritical carbon dioxide fluid varies depending on the type of the very low water-soluble drug. However, the treatment temperature is preferably −40 to 100° C., more preferably 0 to 80° C., particularly preferably 10 to 60° C.

In the present invention, the pressure for treatment with the supercritical or subcritical carbon dioxide fluid varies depending on the type of the very low water-soluble drug. However, the treatment pressure is preferably 1 to 50 MPa, more preferably 1 to 40 MPa, particularly preferably 6 to 30 MPa.

In the present invention, no particular limitations are imposed on the method for producing the composition by use of the supercritical or subcritical carbon dioxide fluid, and the composition is produced through, for example, the following production method: (1) a production method in which the very low water-soluble drug and the present porous material are placed in a pressure-resistant vessel, the vessel is filled with carbon dioxide, the temperature and pressure in the vessel are maintained at a temperature and pressure such that the carbon dioxide is in a supercritical or subcritical state, thereby treating the drug and the porous material with the supercritical or subcritical carbon dioxide, and subsequently the carbon dioxide is discharged from the vessel, followed by collection of the resultant composition; or (2) a production method in which the very low water-soluble drug and the present porous material are placed in a pressure-resistant vessel, the temperature in the vessel is maintained at a temperature at which carbon dioxide is in a supercritical or subcritical state, the vessel is filled with carbon dioxide so as to attain a pressure such that the carbon dioxide is in a supercritical or subcritical state, the drug and the porous material are treated with the supercritical or subcritical carbon dioxide, and subsequently the carbon dioxide is discharged from the vessel, followed by collection of the resultant composition.

The thus-produced very-low-water-soluble-drug-containing composition of the present invention generally has a weight average particle size of 1 μm or more, preferably 1 to 2,000 μm, particularly preferably 3 to 500 μm. The weight average particle size can be measured by means of, for example, laser diffractometry.

When the very low water-soluble drug and the present porous material are treated with the supercritical or subcritical carbon dioxide fluid, if desired, a component which is an acceptable additive in drugs may be added, so long as the component does not impede the effects of the present invention. Examples of the component include a solvent, a polymer compound, and a surfactant.

Examples of the solvent include water; aromatic hydrocarbons such as benzene, toluene, and xylene; ethers such as dimethyl ether, diethyl ether, dioxane, diethoxyethane, tetrahydrofuran, and 1,2-dimethoxyethane; organic-chlorine-containing organic solvents such as dichloromethane, chloroform, carbon tetrachloride, and 1,2-dichloroethane; alkylnitriles such as acetonitrile and propionitrile; nitroalkanes such as nitromethane and nitroethane; amides such as N,N-dimethylformamide and N,N-dimethylacetamide; ketones such as acetone; fatty acids such as acetic acid and oleic acid; alcohols such as methanol, ethanol, and isopropanol; sulfoxides such as dimethyl sulfoxide; and solvent mixtures thereof.

Examples of the polymer compound include pullulan, sodium carboxymethyl cellulose, sodium alginate, xanthan gum, polyvinyl pyrrolidone, carboxyvinyl polymer, methyl cellulose, agar, and gelatin.

Examples of the surfactant include nonionic surfactants such as polyoxyethylene alkyl ethers (e.g., polyoxyethylene polyoxypropylene glycol, polyoxyethylene hydrogenated caster oil, and polyoxyethylene lauryl ether) and sorbitan fatty acid esters (e.g., polyoxyethylene sorbitan fatty acid esters (polysorbate) and sorbitan monostearate).

The very-low-water-soluble-drug-containing composition of the present invention may be employed as pharmaceutical preparations without any treatment, or may be mixed with an additive which is generally employed in pharmaceutical preparations, to thereby prepare an oral drug or a parenteral drug.

Examples of the additive for preparing an oral drug include excipients such as lactose, microcrystalline cellulose, sucrose, mannitol, light anhydrous silicic acid, and calcium hydrogenphosphate; binders such as methyl cellulose, hydroxypropyl cellulose, hydroxypropylmethyl cellulose, gelatin, polyvinyl pyrrolidone, and pullulan; disintegrating agents such as croscarmellose sodium, carmellose calcium, crospovidone, and low-substituted hydroxypropyl cellulose; lubricants such as magnesium stearate and talc; coloring agents such as tar dye and iron sesquioxide; and flavoring agents such as stevia, aspartame, and perfume.

Examples of the additive for preparing a parenteral drug include solvents such as monohydric alcohols (e.g., benzyl alcohol), polyhydric alcohols (e.g., concentrated glycerin and 1,3-butylene glycol), esters (e.g., diisopropyl adipate and triacetin), ketones (e.g., crotamiton), and fats and oils (e.g., oleic acid and caster oil); water-soluble polymers such as celluloses (e.g., hydroxyethyl cellulose and hydroxypropyl cellulose), polysaccharides (e.g., sucrose and β-cyclodextrin), sugar alcohols (e.g., sorbitol and mannitol), and synthetic polymers (e.g., polyvinyl alcohol, polyvinyl pyrrolidone, and polyacrylic acid); surfactants such as anionic surfactants (e.g., calcium stearate, magnesium stearate, and sodium lauryl sulfate), cationic surfactants (e.g., benzalkonium chloride, benzethonium chloride, and cetylpyridinium chloride), and nonionic surfactants (e.g., glyceryl monostearate, sucrose fatty acid ester, polyoxyethylene hydrogenated caster oil, and polyoxyethylene sorbitan fatty acid ester); absorption promoters such as esters (e.g., isopropyl myristate), terpenes (e.g., L-menthol and dL-camphor), and higher fatty acids (e.g., oleic acid); stabilizers such as phenolic substances (e.g., methyl p-hydroxybenzoate and propyl p-hydroxybenzoate), neutral substances (e.g., chlorobutanol and phenylethyl alcohol), invert soaps (e.g., benzalkonium chloride and benzethonium chloride), antioxidants (e.g., vitamin E and butylhydroxyanisole), reducing agents (e.g., ascorbic acid, sodium hydrogensulfite, and sodium thiosulfate), and chelating agents (e.g., citric acid or tartaric acid and salts thereof, lecithin, and ethylenediaminetetraacetic acid (edetic acid)); pH adjusting agents such as phosphoric acid, acetic acid, boric acid, succinic acid, phthalic acid and salts thereof, glycine, and sodium hydroxide; and bases such as (sodium) polyacrylate, polyvinyl pyrrolidone, polyvinyl alcohol, carboxyvinyl polymer, gelatin, and starch.

Examples of the preparation form of the composition of the present invention include oral forms such as a tablet, a capsule, a granule, and a fine granule; and parenteral forms such as an injection, a suppository, a vaginal agent, a sublingual agent, an ointment, a gel formulation, and an implant agent.

EXAMPLES

The present invention will next be described in more detail with reference to Examples and Comparative Examples, but the present invention is not limited to the Examples.

Example 1

Compound A (30 mg), hydrated silicon dioxide (Sylysia 740, product of Fuji Silysia Chemical Ltd.) (300 mg), and dry ice (120 g) were placed in Portable Reactor (product of Taiatsu Techno Corporation), and the reactor was heated to 50° C., to thereby increase the pressure in the reactor to 18 MPa. Subsequently, the temperature and pressure were maintained for five hours under stirring. Thereafter, heating of the reactor was stopped, the reactor was left to cool to room temperature, and the carbon dioxide was discharged from the reactor, to thereby yield a very-low-water-soluble-drug-containing composition.

Example 2

Compound A (30 mg), light anhydrous silicic acid (Sylysia 350, product of Fuji Silysia Chemical Ltd.) (300 mg), and dry ice (120 g) were placed in Portable Reactor, and the reactor was heated to 50° C., to thereby increase the pressure in the reactor to 18 MPa. Subsequently, the temperature and pressure were maintained for five hours under stirring. Thereafter, heating of the reactor was stopped, the reactor was left to cool to room temperature, and the carbon dioxide was discharged from the reactor, to thereby yield a very-low-water-soluble-drug-containing composition.

Example 3

Compound A (30 mg), silicon dioxide (Sylysia 250, product of Fuji Silysia Chemical Ltd.) (300 mg), and dry ice (120 g) were placed in Portable Reactor, and the reactor was heated to 50° C., to thereby increase the pressure in the reactor to 18 MPa. Subsequently, the temperature and pressure were maintained for five hours under stirring. Thereafter, heating of the reactor was stopped, the reactor was left to cool to room temperature, and the carbon dioxide was discharged from the reactor, to thereby yield a very-low-water-soluble-drug-containing composition.

Example 4

Compound A (30 mg), silicon dioxide (Sunsphere H-51, product of Asahi Glass Co., Ltd.) (300 mg), and dry ice (120 g) were placed in Portable Reactor, and the reactor was heated to 50° C., to thereby increase the pressure in the reactor to 18 MPa. Subsequently, the temperature and pressure were maintained for five hours under stirring. Thereafter, heating of the reactor was stopped, the reactor was left to cool to room temperature, and the carbon dioxide was discharged from the reactor, to thereby yield a very-low-water-soluble-drug-containing composition.

Example 5

Compound A (30 mg), calcium silicate (Florite RE, product of Eisai Co., Ltd.) (300 mg), and dry ice (120 g) were placed in Portable Reactor, and the reactor was heated to 50° C., to thereby increase the pressure in the reactor to 18 MPa. Subsequently, the temperature and pressure were maintained for five hours under stirring. Thereafter, heating of the reactor was stopped, the reactor was left to cool to room temperature, and the carbon dioxide was discharged from the reactor, to thereby yield a very-low-water-soluble-drug-containing composition.

Example 6

Compound A (30 mg), light anhydrous silicic acid (Aerosil 300, product of Nippon Aerosil Co., Ltd.) (300 mg), and dry ice (120 g) were placed in Portable Reactor, and the reactor was heated to 50° C., to thereby increase the pressure in the reactor to 18 MPa. Subsequently, the temperature and pressure were maintained for five hours under stirring. Thereafter, heating of the reactor was stopped, the reactor was left to cool to room temperature, and the carbon dioxide was discharged from the reactor, to thereby yield a very-low-water-soluble-drug-containing composition.

Comparative Example 1

Compound A (30 mg) and hydrated silicon dioxide (Sylysia 740, product of Fuji Silysia Chemical Ltd.) (300 mg) were mixed together by use of a mortar, to thereby yield a very-low-water-soluble-drug-containing composition.

Comparative Example 2

Compound A (30 mg) and dry ice (120 g) were placed in Portable Reactor, and the reactor was heated to 50° C., to thereby increase the pressure in the reactor to 18 MPa. Subsequently, the temperature and pressure were maintained for five hours under stirring. Thereafter, heating of the reactor was stopped, the reactor was left to cool to room temperature, and the carbon dioxide was discharged from the reactor, to thereby yield a very-low-water-soluble-drug-containing composition.

<Dissolution Test>

Each of the very-low-water-soluble-drug-containing compositions obtained in Examples 1 through 6 and Comparative Examples 1 and 2 was subjected to dissolution test. The dissolution test was carried out by means of the second dissolution test method (paddle method), which is a general test method specified by Japanese Pharmacopoeia. Specifically, the very-low-water-soluble-drug-containing composition (compound A content: 5 mg) was fed into a test solution (0.3% aqueous sodium lauryl sulfate solution) (900 mL), and subjected to the dissolution test under the following conditions: temperature: 37±1° C., paddle revolutions: 50 r/min.

5 minutes, 30 minutes, 60 minutes, and 120 minutes after initiation of the test, the amount of the compound A dissolved in the test solution was determined by use of a liquid chromatograph employing a reversed-phase column (Inertsil ODS-2, product of GL Sciences Inc.), to thereby calculate percent dissolution (%) of the compound A.

The results are shown in Table 1.

In the very-low-water-soluble-drug-containing composition of Comparative Example 1, the composition being produced through merely physical mixing of compound A with hydrated silicon dioxide, or in the very-low-water-soluble-drug-containing composition of Comparative Example 2, the composition containing no hydrated silicon dioxide and being produced through treatment with supercritical carbon dioxide, virtually no dissolution of the compound A was observed. In contrast, in each of the very-low-water-soluble-drug-containing compositions of Examples 1 through 6, the composition containing compound A and the present porous material (i.e., hydrated silicon dioxide, light anhydrous silicic acid, silicon dioxide, or calcium silicate) and being produced through treatment with supercritical carbon dioxide, dissolution of the compound A was remarkably improved.

Production Example 1

The very-low-water-soluble-drug-containing composition of Example 1 (150 g) was subjected to particle size regulation by use of New Speed Mill ND-02 (product of Okada Seiko Co., Ltd.) equipped with a screen (hole size: 1 mmφ). The resultant composition (110 g), lactose (100-mesh lactose, product of DMV) (42 g), microcrystalline cellulose (Avicel PH-102, product of Asahi Kasei Corporation) (100 g), and low-substituted hydroxypropyl cellulose (L-HPC (LH-11), product of Shin-Etsu Chemical Co., Ltd.) (45 g) were mixed together by use of a V-type mixer for 10 minutes, and subsequently, magnesium stearate (3 g) was added to and mixed with the resultant mixture by use of the V-type mixer for five minutes. The resultant mixture was formed into tablets by use of a tabletting machine (AP-38, product of Hata Iron Works Co., Ltd.), each of the tablets having a weight of 300 mg and containing the compound A in an amount of 10 mg.

Production Example 2

Carboxy vinyl polymer ("Ultrez 10", product of B.F. Goodrich, 1.5 g) and edetate sodium (product of KATAYAMA CHEMICAL INDUSTRIES Co., Ltd., 0.01 g) were added to purified water (40 g), followed by stirring and mixing well. Hydroxypropyl methylcellulose 2906 ("METOLOSE 65SH-1500", product of Shin-Etsu Chemical Co., Ltd., 0.5 g) dissolved in isopropanol (product of Tokuyama Corporation, 20 g) was added to the mixture, followed by further stirring and mixing (aqueous layer). Separately, the composition (11 g) of Example 1, which contained the extremely poorly water-soluble drug, was suspended in polyethylene glycol ("MACROGOL 400", product of NOF CORPORATION, 20 g) (oil layer). The aqueous layer and the oil layer were mixed by an

TABLE 1

| | | Example | | | | | | | | Comparative Example | | | |
|---|---|---|---|---|---|---|---|---|---|---|---|---|---|
| | | 1 | 2 | 3 | 4 | 5 | 6 | 7 | 8 | 1 | 2 | 3 | 4 |
| Compound A (mg) | | 30 | 30 | 30 | 30 | 30 | 30 | 800 | — | 30 | 30 | — | — |
| Prednisolone valerate acetate (mg) | | — | — | — | — | — | — | — | 30 | — | — | 30 | 30 |
| Hydrated silicon dioxide, Sylysia 740 (mg) | | 300 | — | — | — | — | — | — | — | 300 | — | — | — |
| Light anhydrous silicic acid, Sylysia 350 (mg) | | — | 300 | — | — | — | — | 4000 | 300 | — | — | 300 | — |
| Silicon dioxide, Sylysia 250 (mg) | | — | — | 300 | — | — | — | — | — | — | — | — | — |
| Silicon dioxide, Sunsphere H-51 (mg) | | — | — | — | 300 | — | — | — | — | — | — | — | — |
| Calcium silicate, Florite RE (mg) | | — | — | — | — | 300 | — | — | — | — | — | — | — |
| Light anhydrous silicic acid, Aerosil 300 (mg) | | — | — | — | — | — | 300 | — | — | — | — | — | — |
| Dry ice (g) | | 120 | 120 | 120 | 120 | 120 | 120 | — | 120 | — | 120 | — | 120 |
| Liquefied carbon dioxide (g) | | — | — | — | — | — | — | 460 | — | — | — | — | — |
| Average pore diameter (nm) | | 2.5 | 21 | 24 | 5 | 150 | — | 21 | 21 | 2.5 | — | 21 | — |
| Percent dissolution (%) | Stirring time (minutes) 5 | 15.5 | 85.6 | 91.6 | 36.2 | 55.8 | 87.4 | 90.6 | 57.1 | 3.1 | 0.0 | 12.0 | 0.4 |
| | 30 | 42.6 | 96.7 | 96.7 | 77.6 | 61.4 | 92.3 | 97.0 | 83.7 | 5.3 | 1.7 | 37.4 | 0.8 |
| | 60 | 48.9 | 96.8 | 96.9 | 82.4 | 64.7 | 93.6 | 97.0 | 88.0 | 7.5 | 1.1 | 46.0 | 1.3 |
| | 120 | 57.4 | 97.6 | 98.6 | 80.5 | 63.1 | 91.9 | 96.6 | 89.2 | 11.8 | 2.2 | 53.8 | 3.0 |

"AGI HOMO MIXER" (manufactured by PRIMIX Corporation) for 10 minutes under the following conditions: room temperature, 66.7 kPa, 3000 rpm (for homomixer) and 45 rpm (for paddle). Further, diisopropanolamine (product of MITSUI FINE CHEMICALS, INC., 0.7 g) was added to the mixture and filled up to 100 g with purified water, followed by mixing by the AGI HOMO MIXER for 5 minutes under the similar conditions described above, to thereby yield a gel formulation which contained 1 g of Compound A.

Industrial Applicability

By the present invention, a composition, which contains an extremely poorly water-soluble drug and permits excellent dissolution, and its production process can be provided.

The invention claimed is:

1. A composition, comprising:
   a very low water-soluble drug; and
   a porous silicon material;
   wherein:
   the composition is produced by treating a mixture comprising the very low water-soluble drug and the porous silicon material with a supercritical or subcritical carbon dioxide fluid;
   the very low water-soluble drug has a solubility in water at 25° C. of less than 10 μg/mL prior to treatment;
   the porous silicon material comprises at least one member selected from the group consisting of light anhydrous silicic acid, hydrated silicon dioxide, silicon dioxide, and calcium silicate;
   the porous silicon material is not a porous silica material having all of the following:
   an average pore diameter of 1 to 20 nm;
   60% or more of a volume of all of the pores of the porous silica material have a diameter falling within a range of ±40% of the average pore diameter; and
   an X-ray diffraction pattern including one or more peaks at a diffraction angle (2θ) corresponding to d of 1 nm or more;
   the porous silicon material has an average pore diameter of 1 to 500 nm;
   the porous silicon material has a specific surface area of 100 to 1,800 m$^2$/g; and
   the composition is suitable for oral administration.

2. The composition according to claim 1, wherein the porous silicon material has an average pore diameter of 2 to 200 nm.

3. The composition according to claim 1, wherein the porous silicon material has a specific surface area of 200 to 1,500 m$^2$/g.

4. The composition according to claim 1, wherein a ratio by weight of the very low water-soluble drug to the porous silicon material is 1:0.1 to 1:1,000.

5. The composition according to claim 1, wherein the very low water-soluble drug is 2-benzyl-5-(4-chlorophenyl)-6-[4-(methylthio)phenyl]-2H-pyridazin-3-one or prednisolone valerate acetate.

6. A drug product, comprising:
   the composition according to claim 1; and
   at least one additive.

7. A method for producing the composition according to claim 1, comprising:
   placing the very low water-soluble drug and the porous silicon material in a pressure-resistant vessel;
   filling the vessel with carbon dioxide;
   maintaining the vessel at a temperature and pressure such that the carbon dioxide assumes the form of supercritical or subcritical fluid; and
   discharging the carbon dioxide fluid from the vessel and collecting the resultant composition.

8. The method according to claim 7, wherein a ratio by weight of the very low water-soluble drug to the supercritical or subcritical carbon dioxide fluid is from 1:1 to 1:1,000,000.

9. The method according to claim 7, wherein maintaining the vessel comprises maintaining the vessel at temperature of from −40 to 100° C.

10. The method according to claim 7, wherein maintaining the vessel comprises maintaining the vessel at a pressure of from 1 to 50 MPa.

11. The method according to claim 7, wherein the very low water-soluble drug and porous silicon material are maintained in contact with the supercritical or subcritical carbon dioxide fluid for a period of from one minute to 24 hours.

12. A method for producing the composition according to claim 1, comprising:
   placing the very low water-soluble drug and the porous silicon material in a pressure-resistant vessel;
   maintaining the vessel at a temperature at which carbon dioxide is in a supercritical or subcritical state;
   filling the vessel with carbon dioxide so as to attain a pressure such that the carbon dioxide assumes the form of a supercritical or subcritical fluid;
   treating the drug and the porous silicon material with the supercritical or subcritical carbon dioxide fluid; and
   discharging the carbon dioxide fluid from the vessel and collecting the resultant composition.

13. The method according to claim 12, wherein a ratio by weight of the very low water-soluble drug to the supercritical or subcritical carbon dioxide fluid is from 1:1 to 1:1,000,000.

14. The method according to claim 12, wherein treating the drug and the porous silicon material comprises treating at a temperature of from −40 to 100° C.

15. The method according to claim 12, wherein treating the drug and the porous silicon material comprises treating at a pressure of from 1 to 50 MPa.

16. The method according to claim 12, wherein treating the drug and the porous silicon material comprises treating for a period of from one minute to 24 hours.

* * * * *